United States Patent [19]
Fumiyama

[11] Patent Number: 5,989,438
[45] Date of Patent: Nov. 23, 1999

[54] ACTIVE BLOOD FILTER AND METHOD FOR ACTIVE BLOOD FILTRATION

[75] Inventor: Hideo Fumiyama, Irvine, Calif.

[73] Assignee: Baxter International Inc., Deerfield, Ill.

[21] Appl. No.: 08/989,316

[22] Filed: Dec. 12, 1997

[51] Int. Cl.⁶ .............................. B01D 35/00; C02F 1/00
[52] U.S. Cl. ............................ 210/745; 210/85; 604/122
[58] Field of Search .................................. 210/85, 97, 418, 210/420, 739, 745, 746, 767; 604/65, 67, 4, 5, 122; 251/7; 237/599

[56] References Cited

U.S. PATENT DOCUMENTS

| | | |
|---|---|---|
| 3,560,754 | 2/1971 | Kamentsky . |
| 3,791,517 | 2/1974 | Friedman . |
| 3,935,876 | 2/1976 | Massie et al. . |
| 4,014,206 | 3/1977 | Taylor ...................................... 73/19.1 |
| 4,068,521 | 1/1978 | Cosentino et al. . |
| 4,231,366 | 11/1980 | Schael . |
| 4,280,495 | 7/1981 | Lampert . |
| 4,711,715 | 12/1987 | Polaschegg . |
| 4,863,590 | 9/1989 | Ohnishi et al. ........................... 210/93 |
| 4,963,253 | 10/1990 | Yen . |
| 4,966,691 | 10/1990 | Brous . |
| 5,055,198 | 10/1991 | Shettigar . |
| 5,147,544 | 9/1992 | Vescovini . |
| 5,185,086 | 2/1993 | Kaali et al. . |
| 5,188,604 | 2/1993 | Orth . |
| 5,431,811 | 7/1995 | Tusini et al. . |
| 5,478,526 | 12/1995 | Sakai et al. ............................... 422/81 |
| 5,540,841 | 7/1996 | Gsell et al. . |
| 5,605,630 | 2/1997 | Shibata . |
| 5,837,200 | 11/1998 | Diessel et al. . |

FOREIGN PATENT DOCUMENTS 43 26 886  2/1995  Germany .

Primary Examiner—W. L. Walker
Assistant Examiner—Richard W. Ward
Attorney, Agent, or Firm—Guy L. Cumberbatch; Lena Vinitskaya; Yasuo Muramatsu

[57] ABSTRACT

A blood filter is disclosed which actively removes unwanted particles from the blood without using passive elements such as a cartridge. The blood filter includes a housing having a blood inlet area for receiving blood to be filtered, a blood outlet area for providing filtered blood to a patient, and a blood return area for returning blood having unwanted particles to a reservoir. A plurality of independent blood paths extend from the inlet area to the outlet area of the housing for separate flows of blood therethrough. An array of detectors is placed adjacent the exterior of each blood path for detecting unwanted particles in the blood flowing therethrough. An array of valves is placed in operable relationship with the blood paths to close selected ones of the blood paths when unwanted particles are detected. Blood return conduits open to divert the particle-containing blood to a reservoir. Several arrays of detectors and valve combinations may be provided for redundancy. A feedback and control circuit monitors the number of closed blood paths and sends control or alarm signals when the outlet blood flow reduces below a predetermined minimum. A spiral-shaped inlet manifold distributes the incoming blood into different regions corresponding to mass to help improve the efficiency of the filter.

20 Claims, 6 Drawing Sheets

US 5,989,438

ACTIVE BLOOD FILTER AND METHOD FOR ACTIVE BLOOD FILTRATION

FIELD OF THE INVENTION

This invention relates to a blood filter in a bypass circuit for removing particles from blood, and more particularly, to a reduced prime volume active blood filter which actively senses and removes unwanted particles from the blood without a passive filter element.

BACKGROUND OF THE INVENTION

Blood filters are used in a number of medical environments to remove unwanted particulates from a blood stream. For example, an arterial blood filter is commonly used in an extracorporeal circuit for cardiopulmonary bypass surgery to help minimize the dangers of embolism formation. Ordinarily, an arterial blood filter employed in conjunction with an oxygenator system is placed between the oxygenator and patient. Blood is directed from the oxygenator to the filter via a blood pump, and the oxygenated blood is filtered to remove emboli, bubbles, or other particles (generally "particles") before being returned to the patient.

Blood filters used in extracorporeal circuits should have a small priming volume to reduce the trauma to the patient from temporary loss of blood. In addition, extracorporeal filters should be effective in removing all the foreign particles in the blood without an excessive pressure drop, which creates a need for more pump work. Importantly, there should be no, or at least a minimal, chance of blockage, and filter performance should not decrease during the expected useful life of the filter, even during worst case partial plugging of the filter system. Finally, blood filters are disposable and thus should be relatively inexpensive since the filter has to be replaced after every procedure.

In conventional blood filters, a passive element such as a sock-like tubular cartridge, is installed in a generally cylindrical filter housing. Blood enters the housing on an inlet side (inside or outside) of the cartridge and passes through the cartridge walls to the other, outlet side. Because of the large surface area needed to filter an adequate flow of blood, conventional blood filters typically require a priming volume of 200 cc or more, which is proportionally significant in the overall extracorporeal circuit priming volume. Furthermore, fine mesh filter cartridges along with the housings are relatively expensive to continually replace.

Bubble formation may be a problem from the oxygenation process and simple air traps are often used to capture the bubbles before re-entering the patient. Other devices known utilize sensors to detect bubbles in the extracorporeal tubing downstream from the oxygenator. Such sensor devices, however, simply shut off blood flow altogether, or re-rout blood containing bubbles back through a pumping system. See, for example, U.S. Pat. Nos. 4,280,495 and 5,188,604. These setups may detect bubbles, but they also completely disrupt the return blood flow to the patient, which is counterproductive.

In short, there is a need for an effective, inexpensive blood filter with a low priming volume.

SUMMARY OF THE INVENTION

Therefore, it is an object of the present invention to provide a blood filter for use in extracorporeal circuits which is capable of dramatically reducing filter priming volume.

It is another object of the present invention to provide an active blood filter which actively removes particles from the blood without a passive cartridge or membrane.

It is a further object of the present invention to provide an active blood filter having a plurality of blood paths each of which has associated therewith a sensor and a valve controlled by an electric circuit.

It is a further object of the present invention to provide an active blood filter having a plurality of blood paths and a mechanism to ensure that a predetermined number of blood paths remain open to supply an adequate flow of blood to the patient.

It is a further object of the present invention to provide an active blood filter of low cost and high performance where a housing of the filter including a plurality of blood tubes is disposable while external detectors and valves can be re-used.

In the first aspect of the present invention, the blood filter includes a housing having a blood inlet area for receiving blood to be filtered, a blood outlet area, and a blood return area for returning blood having unwanted particles to a reservoir. A plurality of separate blood paths extend from the inlet area to the outlet area of the housing for flowing the blood therethrough. Each of the blood paths includes a detector adjacent to the blood path for detecting unwanted particles in the blood flowing through the blood path, and a valve in operable relationship with the blood path for closing the blood path when an unwanted particle is detected by the detector.

Another aspect of the present invention is a method of filtering including the steps of supplying blood to an inlet of a blood filter housing having a blood outlet and a blood return, flowing the blood through a plurality of separate blood paths extending from the inlet to the outlet of the blood filter housing, detecting unwanted particles in the blood flowing through the blood paths and generating signals upon detection of particles; and closing selected ones of the blood paths based on the signals and returning the blood to a reservoir through the blood return.

BRIEF DESCRIPTION OF THE DRAWINGS

FIG. 1b is an upper portion of FIG. 1a.

FIG. 1c is a lower portion of FIG. 1a.

DESCRIPTION OF THE PREFERRED EMBODIMENTS

The present invention provides an active blood filter which is useful in any environment in which blood is filtered, but particularly in extracorporeal circuits where a low prime volume is extremely desirable. For example, cardiopulmonary bypass circuits typically require filtering after collection, defoaming and oxygenation to remove unwanted particles not trapped in the venous reservoir or oxygenator. Unwanted particles in this sense includes bone and tissue fragments, emboli, bubbles, and the like. The present invention separates the blood into a plurality of paths and monitors each path for unwanted particles. The monitoring can be done with a single sensor per blood path, or multiple sensors. Various sensors may be used for this purpose, and the invention should not be limited to any one sensor. Furthermore, the number and configuration of the blood paths should be viewed as exemplary only, and other configurations are within the scope of the invention. Finally, the present filter is illustrated and described as part of a cardiopulmonary bypass circuit with a return conduit to a venous reservoir. Those of skill in the art will recognize that the particle-containing blood can be returned to other "reservoirs", including the inlet of the filter itself for a second pass therethrough. Thus, the use of the term "reservoir" should not be construed as limiting.

Figure 1A:
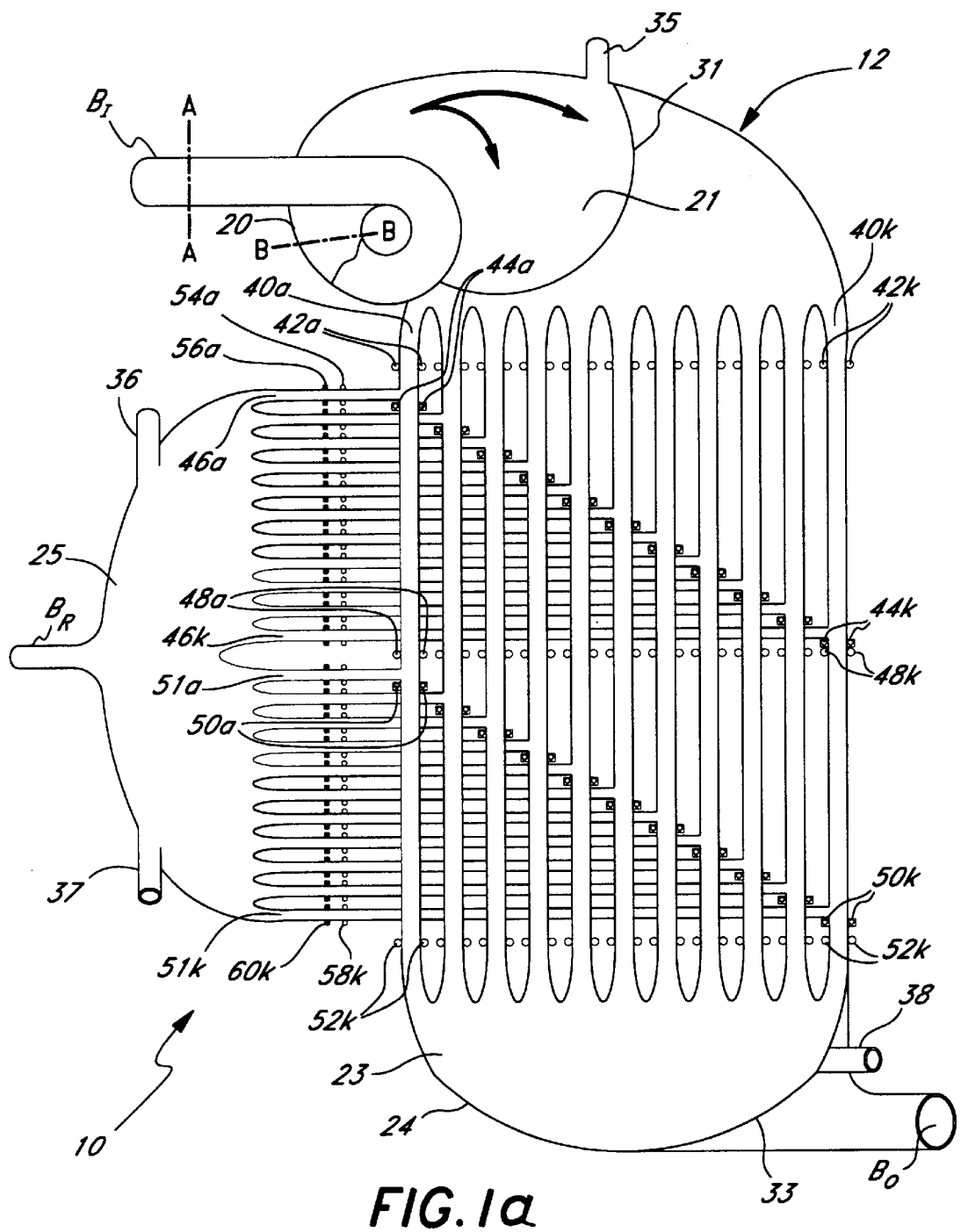
FIG. 1a is a schematic diagram showing a front cross-sectional view of an active blood filter of the present invention.
Figure 2:
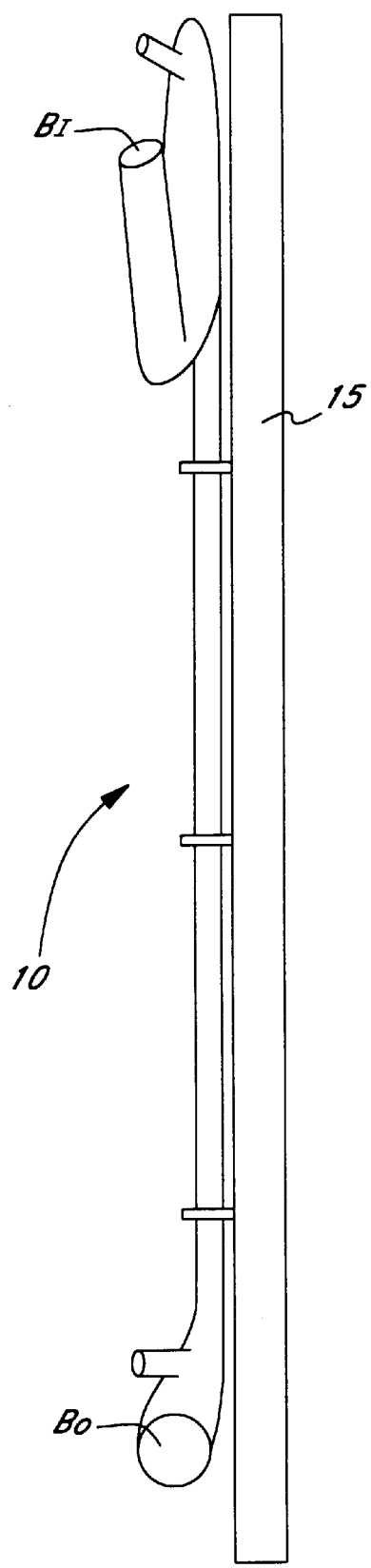
FIG. 2 is a side view of the active blood filter of the present invention.

FIGS. 1a and 2 show an active blood filter 10 of the present invention in both front cross-sectional and side elevational views. The filter 10 preferably has a generally flat shape in profile and is attached to a holder 15 for stability. The holder 15 may be, for example, a stand or a bracket structure for clamping the filter 10 to a vertical pole (not shown). Desirably, the filter 10 functions as shown with a plurality of vertically and horizontally oriented blood paths. In this manner, the inherent potential energy of the blood assists in its flow through the filter 10. Of course, other configurations making use of pumps and the like may be substituted.

As mentioned, and as seen in FIG. 1a, the blood filter 10 has a plurality of blood paths, i.e., tubes, for allowing blood to pass therethrough. A housing 12 of the blood filter 10 defining the blood paths is made, for example, of polycarbonate and sealed from the exterior. Each of the blood paths may be integrally formed with the housing 12, or may be separately formed and made of, for example, PVC (Polyvinyl Chloride). In the latter case, each tubular blood path may be closed by a small clamping force externally provided thereto, such as with typical surgical clamps. Other valve arrangements may be substituted, but externally provided clamps enables their removal and subsequent re-use, thus reducing the cost of the disposable portion of the filter 10.

An inlet $B_I$ introduces blood to be filtered to the upper end of the housing 12, while an outlet $B_O$ in the lower end supplies the filtered blood to a patient, or other recipient. A blood return outlet $B_R$ from the housing 12 provides a return path for blood containing unwanted particles to a reservoir (not shown). Again, the reservoir may be a venous reservoir, another filter, or even the inlet $B_I$.

The inlet $B_I$ begins as a tubular shape to mate with conventional blood tubing and gradually expands through a spiral inlet manifold 20 as seen in the front view of FIG. 1a into a top space 21 of the housing 12. Conversely, a bottom space 23 of the housing converges in front view along a rounded bottom wall 24 to the tubular outlet $B_O$. Similarly, the tubular blood return outlet $B_R$ communicates with a wider return space 25. Preferably, air traps 31 and 33 are provided in the housing 12 within the top space 21 and the bottom space 23, respectively. The air traps 31 and 33 may be conventional screen-like devices known in the art for intercepting and bursting microbubbles in blood. Also, the air traps 31 and 33 intercept large thrombus formations. Air ventilators 35 and 38 are provided for releasing and air created by the air traps 31 and 33, while ventilators 36 and 37 are provided for the return space 25. It should be noted, however, that if the detectors for particles described below are sensitive enough to detect microbubbles, then the air traps 31 and 33 may not be needed.

The blood filter 10 includes a plurality of blood paths 40a through 40k (collectively "40") having upper ends in fluid communication with the upper space 21 (after the air trap 31). In an exemplary embodiment, the blood path upper ends extend in series beginning adjacent the spiral manifold 20 and continuing away from the manifold to a distal side of the space 21. In the illustrated embodiment there are eleven blood paths 40a–40k, although other numbers are contemplated. The blood paths 40 are preferably tubular and extend in a vertical direction the length of the housing 12 to lower ends open to the lower space 23. A downstream direction is thus defined through the blood paths 40 from the inlet space 21 to the outlet space 23.

At an inlet area of the blood paths 40, a first array of detectors 42a through 42k (collectively "42") is provided adjacent each blood path. The detectors 42 are positioned close to the inlet end of the blood paths 40 along a horizontal line, but of course other arrangements are possible. The detectors 42 are arranged at the outside of the blood paths 40 in a manner so as to be easily disconnectable therefrom. For example, the detectors 42 may be connected together in a string, and each detector may be fitted with a U-shaped clamp for fitting around the tubular blood paths 40. In this manner, the entire string of detectors 42 can be installed at once. The detectors 42 are designed to monitor the blood paths 40 for foreign particles, and to send an output signal when particles are found. Although not shown, appropriate wiring is used to activate and/or monitor the detectors 42. Typically, the detectors are photo sensors each of which has at least an LED (Light Emitting Diode) and a photo diode to detect particles in the blood flowing in the tube. Other sensors such as ultrasonic sensors for sensing acoustic anomalies in the blood or impedance sensors for sensing impedance of the blood flow are also feasible to detect the particles.

Figure 3:
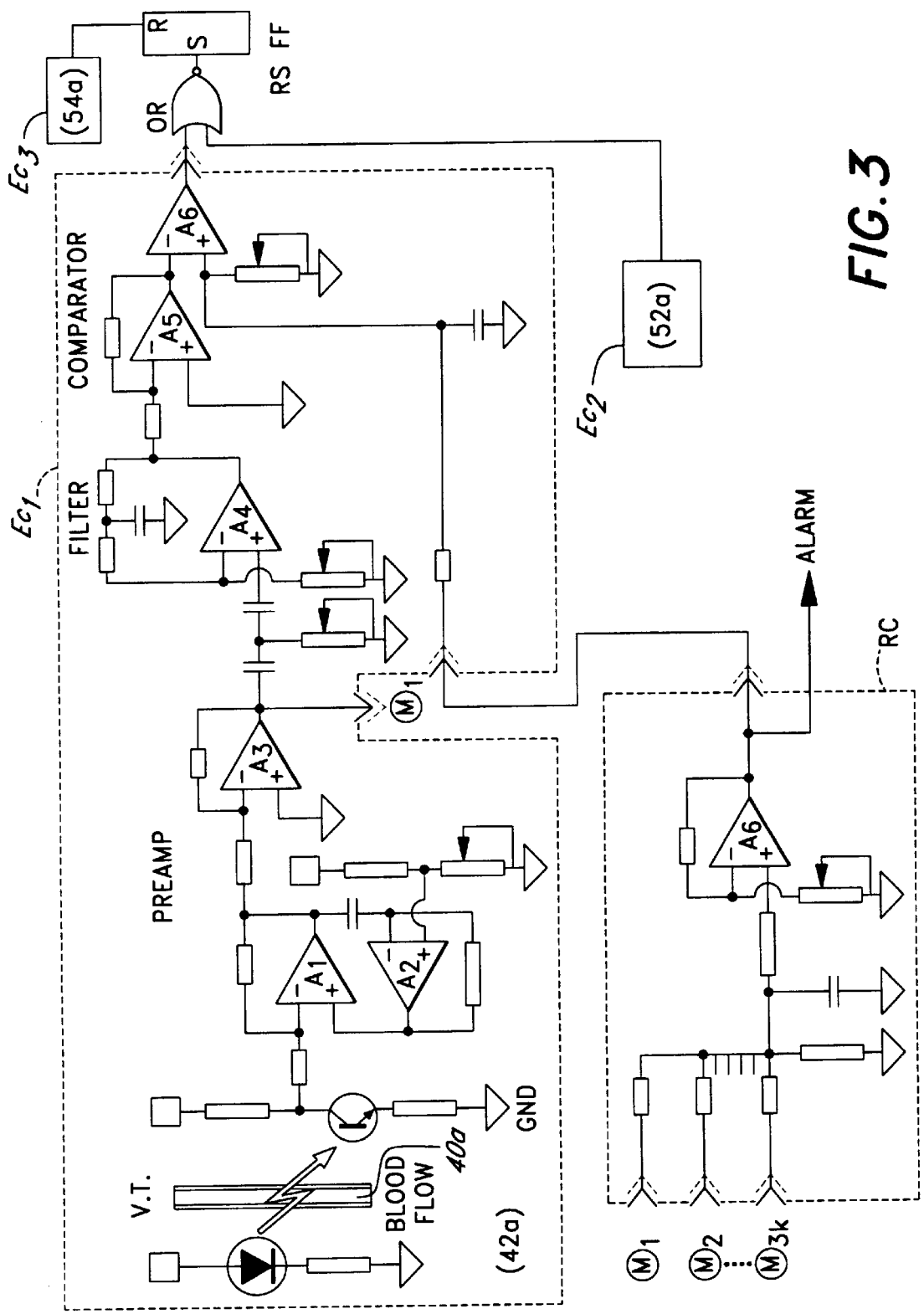
FIG. 3 is a diagram showing an example of electronic circuits to be used in conjunction with the active blood filter of the present invention.

A first array of valves 44a–44k (collectively "44") is provided in operative relationship with the blood paths 40 at positions downstream from the detectors 42. The valves 44 are arranged at the outside of the blood paths 40 in a manner easily disconnectable therefrom. As shown in FIG. 1a, the valves 44 are arrayed diagonally across the blood paths 40 and just below first blood return conduits 46a–46k which communicate with the return space 25. There is one detector 42 and valve 44 combination per blood path 40. Both the first array of detectors 42a–42k and the first array of valves 44a–44k are connected to an electric circuit such as shown in FIG. 3 to perform an active filtering operation as will be described later.

Figure 4:
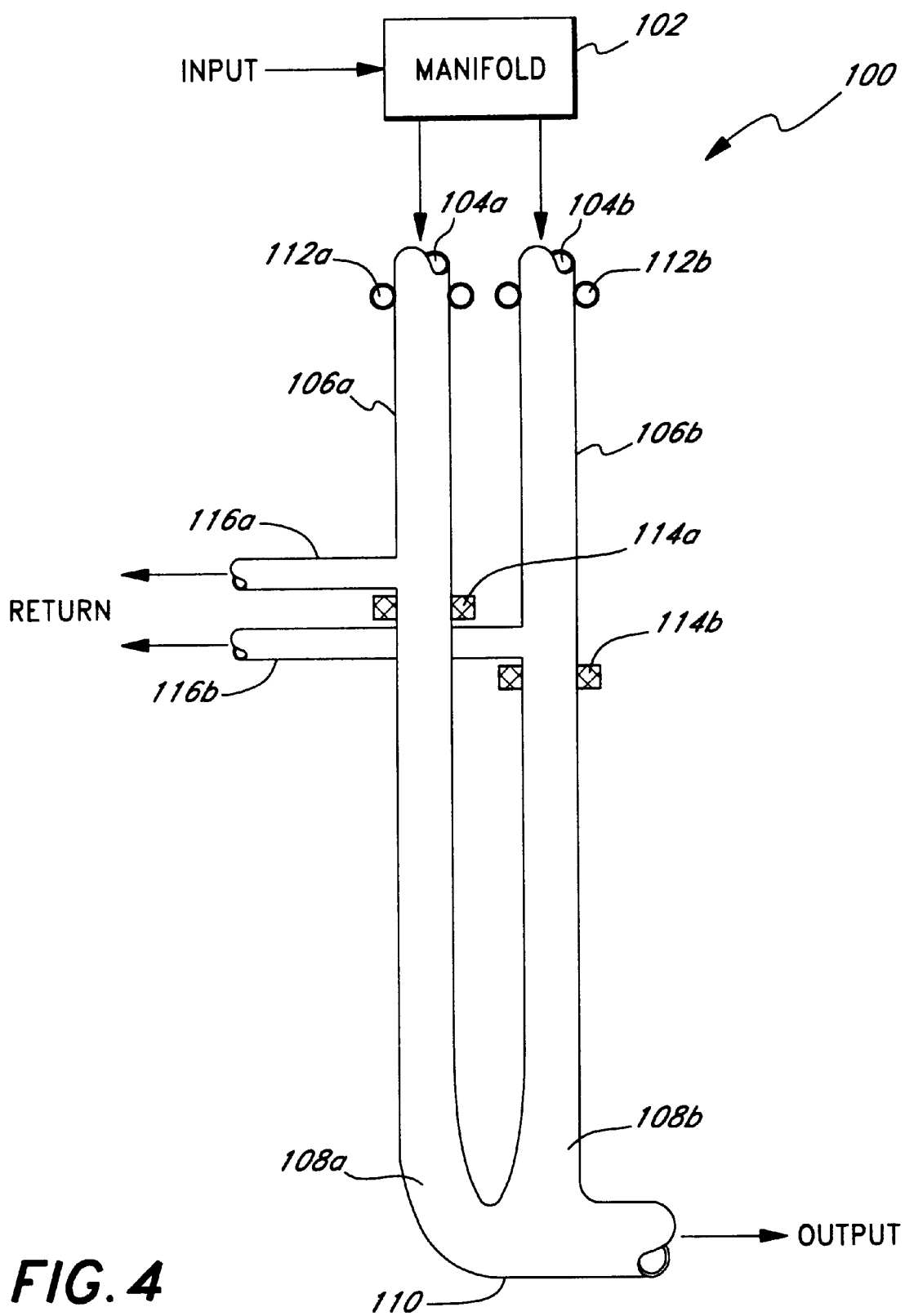
FIG. 4 is a schematic diagram of an exemplary active blood filter of the present invention.

In the preferred embodiment, the sensitivity and efficacy of a single sensor placed adjacent each blood path is sufficient to intercept and divert any particles in the blood stream. FIG. 4 (described below) illustrates a simple system in accordance with the present invention which utilizes only one sensor and valve per blood path. In some situations, however, more than one sensor per blood path may be indicated, and the filter 10 illustrates such a design as follows.

Downstream from the first array of valves 44 and adjacent the blood paths 40, a second array of detectors 48a–48k (collectively "48") is provided. In conjunction with the detectors 48, a second array of valves 50a–50k (collectively "50") is provided in operable relationship with the blood paths 40 at positions downstream from the detectors 48. Both the detectors 48 and valves 50 are desirably arranged on the exterior of the blood paths 40 in a manner easily disconnectable therefrom. In this manner, the blood paths 40 are disposable while the hardware of the detectors and valves may be reused. The valves 50 are arrayed diagonally across the blood paths 40 and just below second blood return conduits 51a–51k which communicate with the return space 25.

A third array of detectors 52a–52k (collectively "52") is provided adjacent to the blood paths 40 downstream from the second array of valves 50 and close to the bottom space 23.

The first return conduits 46a–46k correspond to the first array of valves 44a–44k and second blood return conduits 51a–51k correspond to the second array of valves 50a–50k. In the exemplary embodiment, there are the same number of valves 44 as there are valves 50 (corresponding to the number of blood paths 40), and thus the same number of first and second blood return conduits 46 and 51. Of course, there may be other arrangements.

As mentioned, the ends of the return conduits 46, 51 are open to the return space which is connected to the reservoir through the outlet $B_R$. Each blood return conduit 46, 51 is desirably oriented horizontally and intersects the blood paths 40 perpendicularly at a T-junction. The return conduits 46a–46k are provided with a fourth array of detectors 54a–54k (collectively "54"), and a third array of valves 56a–56k (collectively "56") at positions closer to the return space 25. Likewise, the return conduits 51a–51k are provided with a fifth array of detectors 58a–58k (collectively "58"), and a fourth array of valves 60a–60k (collectively "60") at positions closer to the return space 25.

Operation

Operation of the active blood filter of the present invention will now be described. Basically, the blood filter of the present invention actively detects unwanted particles in the blood and reacts by diverting the particles away from the patient, or other recipient. In a cardiopulmonary bypass environment, the particle-containing blood is diverted back to the venous reservoir, and from there goes through an oxygenator, a pump and back to the inlet of the filter. Whatever particle is detected is desirably intercepted outside of the filter by one of these extracorporeal devices, or is then detected and diverted again.

In an optimal operating condition, with blood flowing through all of the blood paths 40a–40k, the first array of valves 44a–44k and the second array of valves 50a–50k are open, while the third array of valves 56a–56k and the fourth array of valves 60a–60k are closed. Thus, blood continues through all blood paths 40 from inlet space 21 to outlet space 23 without being diverted.

The blood enters blood inlet $B_I$, travels around spiral manifold 20 and passes through the air trap 31 which substantially removes air bubbles in the blood. The air collected from bursting bubbles will go out of the blood filter 10 through the air ventilator 35.

Figure 1B:
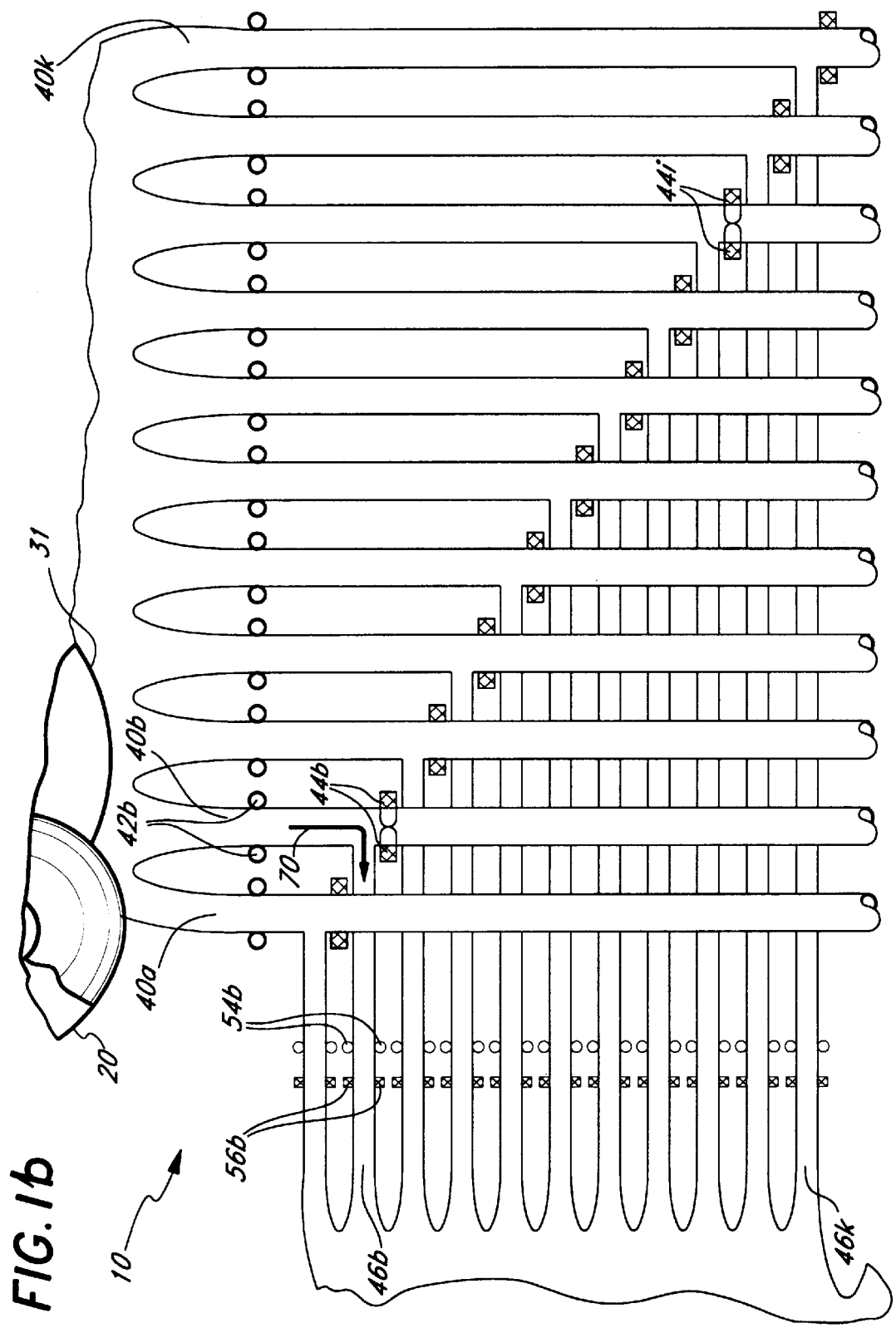

With reference now to FIG. 1b, the blood falls by gravity and is separated to flow through the independent blood paths 40a–40k. The first array of detectors 42a–42k monitors the incoming blood for particles. If an unwanted particle is detected by one of the first array of detectors, such as the detector 42b, the blood path 40b is clamped by the valve 44b. At the same time, the valve 56b is opened thus diverting flow through the blood return conduit 46b, as indicated by arrow 70.

The blood containing the unwanted particle is returned to the reservoir through the outlet $B_R$. The detector 54b monitors the blood return conduit 46b to sense when the particle passes toward the outlet $B_R$, and sends a detection signal to an electric circuit to release the valve 44b and close valve 56b so that the blood path 40b is open again. The proximity of the sensor 54b to the valve 56b and the circuit timing ensures that the particle passes the valve before it closes.

Figure 1C:
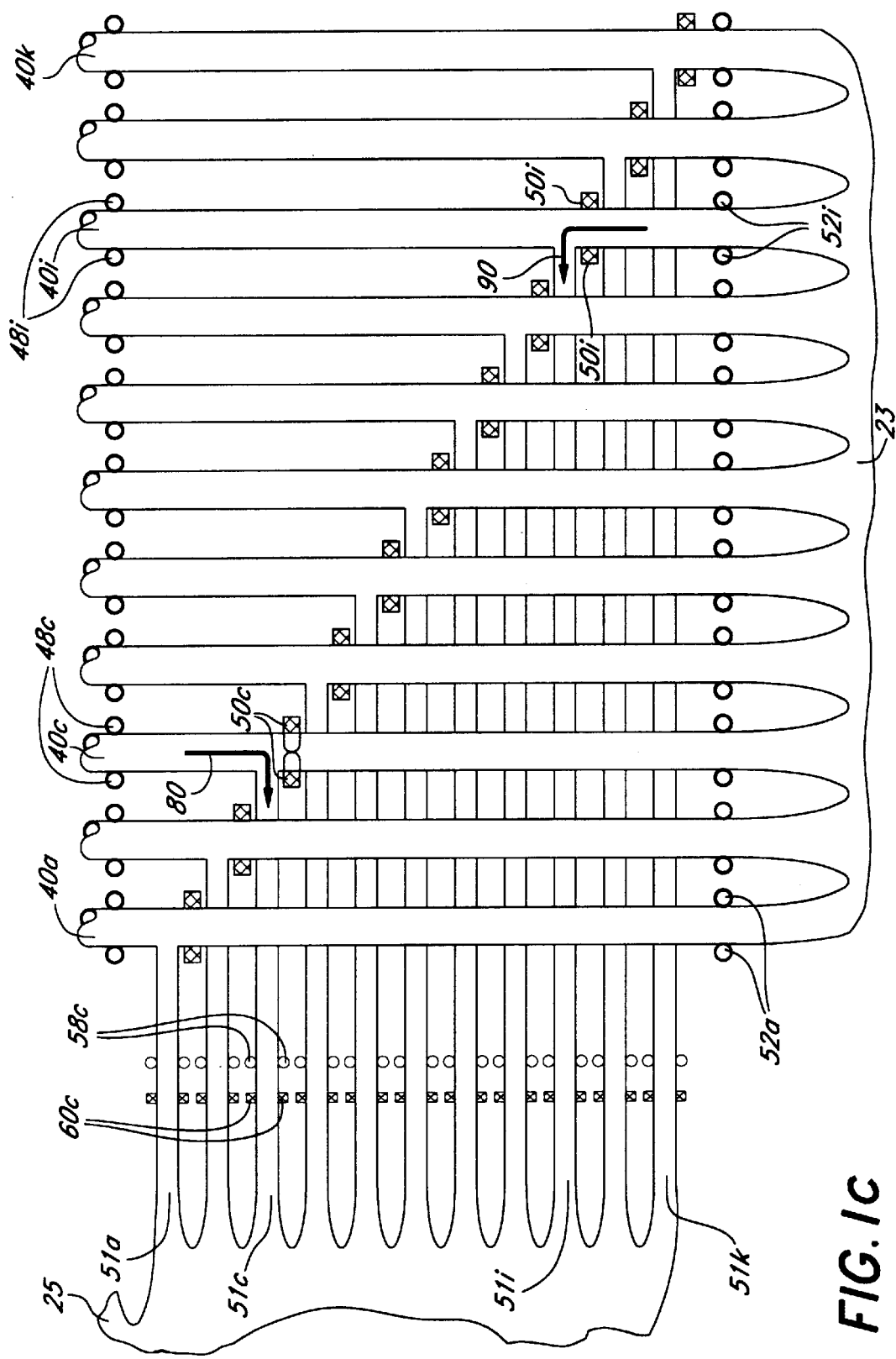

If no particles are detected in any of the blood paths 40, the blood goes down to the lower half of the blood paths 40 and passes through the second array of detectors 48a–48k, as seen in FIG. 1c. The detectors 48 monitor the blood flowing through the corresponding blood paths 40 and send detection signals when any unwanted particles are detected which are not caught by the first array of detectors 42. Thus, the second array of detectors 48 lends some redundancy to the filter 10. Alternatively, the first array of detectors 42 may be differently calibrated than the second array 48 to detect larger particles. In this manner, and with some empirical testing, a system of cascading arrays of detectors can be customized for a particular volumetric flow and size of filter, for example. In any event, multiple arrays of detectors for each blood path 40 adds security for the recipient.

For example, if a particle flowing through the blood path 40c is not detected by the detector 42c in the first array of detectors 42, it may now be detected by the detector 48c. The detector 48c sends a detection signal to close the circuit which closes the valve 50c and opens the valve 60c. This sequence closes the blood path 40c below the valve 50c and opens the return conduit 51c. Blood is diverted as indicated by arrow 80 through the return conduit 51c to the return space 25. As a consequence, blood containing the unwanted particle is returned to the reservoir through the outlet $B_R$. The detector 58c monitors the return conduit 51c to confirm that the particle passes therethrough toward the outlet $B_R$, and sends a detection signal to the electric circuit to release the valve 50c and close valve 58c so that the blood path 40c is open and undiverted again.

Again, the present invention is intended to provide an effective and inexpensive blood filtering system, and two arrays of detectors and accompanying valves is believed sufficient to intercept all particles which may pose a threat to the blood recipient. However, if desired, the present invention illustrates additional redundancy for detecting and diverting particles which have not been detected by either of the first or second arrays of detectors 42, 48. Namely, the third array of detectors 52a–52k, the first and second array of valves 44 and 50, and the return conduits 46 and 51, along with the fourth array of valves 60a–60k.

Thus, with reference to FIG. 1c, if the detector 52i, which is place at a position close to the bottom space 23, senses a particle in the blood path 40i it generates a detection signal. Upon receipt of the detection signal, the circuit closes the valve 44i in the upper position of the blood path 40i (FIG. 1b), and opens the valve 50i in the intermediate position of the blood path. Also, the circuit opens the valve 60i in the return conduit 51i. Since the pressure in the outlet space 23 is higher than that in the return space 25 connected to the outside reservoir, the blood just past the detector 52i reverses its direction and flows in the upward direction of the blood path 40i, and through the return conduit 51i to the reservoir, as indicated by arrow 90. This prevents the unwanted particle from being outlet from the filter 10. Again, the distance from the detector 52i to the outlet space 23 is such that the circuit can catch any particle sensed thereby and divert it before it leaves the blood path 40i.

Alternatively, a valve (not shown) can be positioned downstream of each detector 52 to halt any particles sensed thereby from continuing to the outlet space 23. Still other variants will be apparent to one of skill in the art, and the third array of detectors 52a–52k is illustrated solely to explain that more than two sensors per blood path may be used. The specific system implemented should be well tested to ensure that no particles can escape from the filter without being diverted back to the reservoir.

Particle Sorting

The inlet manifold 20 of the blood filter 10 is spirally formed as shown in FIG. 1a so that rotation of the blood is induced through the spiral path before being provided to the upper space 21. In this manner, blood introduced at the inlet $B_I$ is given a rotational component of motion and accompanying radial and tangential momentum before entering upper space 21 of the blood filter 10. It will be noted that in the preferred embodiment the manifold changes cross-sectional shape from circular at the blood inlet $B_I$ to generally oval or elongated at the point of entry to the inlet space 23. At the same time, the cross-sectional area of the inlet manifold remains constant. Thus, with reference to FIG. 1a, the manifold 20 has a circular cross-section at A—A, and an elongated cross-section B—B. The elongation is in the plane of the page, and thus the manifold 20 narrows in the direction in and out of the page. The constant cross-section ensures that the flow experiences no expansion or contraction through the manifold, thus avoiding pressure discontinuities. In addition, as described below, the manifold cross-sectional area is desirably equal to or less than the combined cross-sections of the average number of blood paths 40 open during use of the filter 10, thus ensuring minimal pressure drop through the filter.

The incoming blood has a predetermined pressure generated by a blood pump (not shown) provided before the blood filter 10, which causes a predetermined rotational blood speed in the spiral manifold 20 which can be adjusted by the pump pressure, manifold size, manifold curvature, etc. The momentum of each blood particle causes it to conform to the upper wall of the housing 12. Heavier particles tend to travel farther along the upper wall because of their higher momentum, while lighter particles succumb sooner to gravity and fall toward the open upper ends of the blood paths 40. In this situation, blood having the same or similar masses of particles tends to falls in a similar group of blood paths 40. For example, foreign particles in the blood, typically being heavier than the surrounding blood, tend to be distributed farther from the inlet manifold 20, to the right in FIG. 1a. This phenomenon increases the likelihood of detecting particles in the blood paths 40 farther from the inlet manifold 20, which concentrates the blood path closures and minimizes the average number blood paths closed at any one time. Other arrangements for sorting the incoming blood in this manner are contemplated.

Feedback and Control

FIG. 3 is a circuit diagram showing an example of electronic circuits to be used in the active blood filter of the present invention. The circuit diagram of FIG. 3 shows electric circuits mainly corresponding to a combination of the detectors and the valves in the upper position of the blood path 40a. An electric circuit $Ec_1$ is for receiving a detection signal from the detector 42a on the blood path 40a and drives the valve 44a to close the blood path 40a.

In the electric circuit $Ec_1$, the detector 42a is formed of an LED and a photo diode PD. The light from the LED passes through the blood in the blood path 40a and is sensed by the photo diode PD. If a particle is included in the blood, a power level received by the photo diode PD changes (detection signal) which is amplified by a PREAMPLIFIER formed of operational amplifiers $A_1$–$A_3$.

Preferably, the electric circuit $Ec_1$ includes a noise FILTER formed of an operational amplifier $A_4$ and other passive components to remove noise superimposed on the detection signal. Typically, such noise is stray noise caused by a 60 Hz commercial electric power source. Thus, the frequency of the noise filter is set to approximately 60 Hz to remove the noise. The output of the preamplifier is thus applied to the noise filter as shown. Also, the output of the preamplifier is provided to a reference circuit RC in the lower part of FIG. 3.

The detection signal from the noise filter is provided to a COMPARATOR formed with operational amplifiers $A_5$–$A_6$ where it is compared with a reference voltage from the reference circuit RC. If a voltage level of the detection signal is greater than the reference voltage, an output signal is generated by the comparator for driving a corresponding valve, in this case, the valve 44a. If the reference voltage is larger than the detection signal, an output signal is not produced by the comparator and the valve 44a will remain open.

The reference circuit RC receives the detection signal from the electric circuit $Ec_1$ which processes the signal from the photo diode forming the detector 42a. The reference circuit RC also receives other detection signals corresponding to other detectors in the blood filter of the present invention (currently shown as 3k, where k is the number of blood paths). The purpose of the reference circuit RC is to detect the number of blood paths generating detection signals at the same time. When the number of blood paths that are to be closed exceeds a predetermined number, the reference voltage for the amplifier $A_6$ is increased to be sufficiently larger than the detection signal. As a result, this arrangement ensures that a predetermined number of blood paths remain open so that an adequate blood flow for the patient is maintained even though the blood contains the unwanted particles. This is a worst case scenario, and with appropriate design of the filter 10 would not likely happen.

The reference circuit RC is an adder circuit formed of an operation amplifier $A_7$ whose output voltage proportionally increases with the increase of input signals. Thus, the output voltage of the reference circuit is connected to the comparator in the electric circuit $Ec_1$ as the reference voltage. The output voltage may also be provided to other means such as a speaker or a light source to generate alarm sound or alarm light showing that unwanted particles are sensed in more than a predetermined number of blood paths.

The output of the comparator in the electric circuit $Ec_1$ is connected to an OR gate whose another input is connected to an output of another electric circuit $Ec_2$. The output of the OR gate is connected to a set terminal of an RS flip flop which drives the valve 44a. A reset terminal of the RS flip flop is connected to an electric circuit $Ec_3$.

Each of the electric circuits $Ec_2$ and $Ec_3$ has substantially the same circuit arrangements as in the electric circuit $Ec_1$. The electric circuit $Ec_2$ includes the detector 52a which is one of the third array of detectors attached on the blood path 40a close to the bottom space 23. As described in the foregoing, when the particle is detected by the detector 52a, the blood that has passed through the detector $52_1$ is controlled to flow in the reverse direction toward the reservoir by closing the valve 44a. This is achieved by connecting the output of the electric circuit $Ec_2$ to the OR gate so that the valve 44a closes by the detection signals either from the electric circuit $Ec_1$ or $Ec_2$.

The electric circuit $Ec_3$ includes the detector 54a which is one of the fourth array of detectors provided for the return conduits 46. As described in the foregoing, when the particle is found by the detector 42a in the blood flowing through the blood path 40a, the valve 44a closes the blood path to flow the blood toward the reservoir through the return conduit 46a. The detector 54a monitors the flow of the blood, and when the particle has passed the return conduit 46a, it sends a detection signal to open the blood path 40a. This is achieved by connecting the output of the electric circuit $Ec_3$ to the reset terminal of the RS flip flop to release the valve 44a.

Although the electric circuit is explained only with reference to upper part of the blood path 40a, the same or similar circuit arrangements can be used for the lower part.

Exemplary Active Blood Filter

FIG. 4 illustrates an active blood filter 100 in which an inlet blood flow enters a flow manifold 102. As mentioned above, the inlet can be from an oxygenator via a blood pump, or other such expedient. The manifold 102 may be designed to distribute (or sort) blood flow according to weight, or by some other criteria, or may be a simple flow divider. The blood is divided by the manifold 102 and enters open first ends 104a, 104b of two blood paths 106a, 106b. The blood paths 106a,b continue for a predetermined length and terminate at second ends 108a, 108b converging in an outlet manifold 110. From there, the blood outlets to a recipient, such as a patient undergoing bypass surgery.

At a predetermined location along each blood path 106a, b, a particle detector 112a, 112b is positioned. In the illustrated embodiment, the detectors 112 are positioned proximate the first ends 104, but they are desirably positioned upstream of diverter valves 114a, 114b. The valves 114 are adapted to close flow through the paths 106, and through associated return paths 116a, 1161b. The return paths 116 converge in a reservoir or other common container, as described, and may be routed back through an oxygenator system to the inlet.

Thus, the simple blood filter 100 includes a single detector and diverter valve pair for each separate blood flow path. Those of skill in the art will recognize that any number of blood flow paths may be combined in this manner to further divide and filter the blood flow. Furthermore, the configuration of each blood flow path, detector, and diverter valve may differ from one another if desired.

According to the present invention, an active blood filter removes particles in the blood without using a passive element like a mesh screen or cartridge. In an exemplary embodiment, with eleven blood paths, the blood filter of the present invention achieves a priming volume of approximately 69 cc for adults and 29 cc for pediatrics, which is remarkably smaller than the conventional blood filter.

As in the foregoing, the active blood filter of the present invention has a plurality of blood paths and return conduits. Each of the blood paths is provided with a detector and a valve. If a particle exists in the blood, the detector sends a detection signal so that the valve closes the blood path. At the same time, the return conduit is opened by a valve provided thereto so that the blood containing the particle is diverted to a reservoir. Preferably, the blood filter further includes another detector and a valve in the same blood path to remove particles not diverted by the first set. Furthermore, preferably, the blood filter of the present invention includes a detector to detect a particle at the outlet area of the filter so that the blood flows in the reverse direction and is diverted to the reservoir.

Since the blood filter should impose a minimum pressure drop to the blood flow, the relative sizes of the blood inlet $B_I$ and the combined blood paths $40a$–$40k$ should be selected to meet a certain relationship. That is, the cross-sectional area of the blood inlet $B_I$ and manifold 20 is desirably equal to or less than the combined cross-sections of the average number of blood paths 40 open during use of the filter 10, thus ensuring no constriction of flow and minimal pressure drop through the filter. Using the illustrated example, if two (2) out of eleven (11) blood paths 40 are closed at the same time on average, the surface area of the blood inlet $B_I$ is set to substantially equal to the sum of surface areas of nine (9) blood paths 40. Under this relationship, and assuming an average number of blood path closures, the blood flow will not be reduced by the filter. Empirical testing may be used to determine an average number of blood path closures during use of the filter 10, which can in turn be used to set the number of blood paths and their sizes relative to the blood inlet $B_I$.

In an exemplary embodiment of a filter 10 for use on adult patients, the tubular inlet $B_I$ has an inner diameter of ⅜ inch, and each of the blood flow paths 40 is tubular with an inner diameter of ⅛ inch. Thus, nine of the blood flow paths 40 has the same cross-sectional area as the inlet $B_I$. If eleven paths 40 are provided, then two can be closed with no reduction in cross-sectional flow area through the filter 10. The same can be done with smaller inlets, such as ¼ or 3/16 inch inlets typically used for infants and pediatric patients. The smaller the blood path 40, the easier in general to sense for particles, and ⅛ inch is by no means the minimum size contemplated, although there is a trade off with the expense of providing increasing numbers of blood paths and accompanying hardware.

In the present invention, it is desirable that the housing and all of the blood paths of the blood filter are disposable while all of the detectors, valves and electric circuits may be re-used. Therefore, the detectors and the valves are so structured to be easily attachable to the outer surfaces of the blood paths as well as easily be detachable therefrom. For simplicity of installation, the frame 15 may have the various detectors and valves mounted thereon, and have appropriate clamps, brackets, and layout diagrams for easily coupling the disposable tubes to the re-usable hardware.

Finally, each of the valves clamps the tube to close the blood path when a drive signal is provided thereto. Such valves can be any mechanical dampers driven by electric signals. Other types of valves such as solid state valves formed with piezoelectric elements are also feasible.

It is understood that the examples and embodiments described herein and shown in the drawings represent only the presently preferred embodiments of the invention, and are not intended to exhaustively describe in detail all possible embodiments in which the invention may take physical form. Indeed, various modifications and additions may be made to such embodiments without departing from the spirit and scope of the invention.

What is claimed is:

1. A blood filter for removing unwanted particles from blood, comprising:
   a housing having a blood inlet area for receiving blood to be filtered, a blood outlet area, and a blood return area for returning blood having unwanted particles to a reservoir;
   a plurality of separate blood paths extending from the inlet area to the outlet area of the housing for flowing the blood therethrough, wherein each of the blood paths includes:
      a detector adjacent to the blood path for detecting unwanted particles in the blood flowing through the blood path;
      a valve in operable relationship with the blood path for closing the blood path when an unwanted particle is detected by the detectors; and
   a circuit for limiting the number of the valves that close to ensure an adequate blood flow from the intlet to the outlet of the filter.

2. A blood filter as defined in claim 1, further comprising:
   a plurality of return conduits, one return conduit connecting to each of the blood paths and extending to the blood return area of the housing to allow blood having unwanted particles to flow to the reservoir, wherein each of the return conduits includes:
      a detector adjacent to the blood return conduit for monitoring the unwanted particles in the blood flowing through the blood return conduits; and a valve in operable relationship with the blood return conduit for opening the blood return conduit and for enabling blood having an unwanted particle to flow to the reservoir.

3. A blood filter as defined in claim 1, wherein the inlet area of the housing has a spiral structure to impart momentum to blood entering the housing so that the blood is distributed to the plurality of blood paths based on the momentum of the particles.

4. A blood filter as defined in claim 1, wherein an average number of blood paths closed at any one time is predetermined, and the inlet cross-sectional area of the housing is substantially the same as a sum of the cross-sectional areas of all of the plurality of blood paths less the cross-sectional areas of the predetermined average number of blood paths closed at the same time by the valves.

5. A blood filter as defined in claim 1, further comprising:
   an amplifier for amplifying a detection signal generated by each of the detectors and driving a corresponding one of the valves; and
   means for detecting a number of detection signals from the detectors and prohibiting further closing of the blood paths by the valves when the number of the detection signals reaches a predetermined value.

6. A blood filter as defined in claim 1, wherein each of the blood paths is a tube made flexible enough to be physically squeezed shut to substantially prohibit blood from flowing when an external clamping force is applied thereto.

7. A blood filter as defined in claim 1, wherein each of the detectors is a combined LED and a photo diode for sensing light power changes through the blood.

8. A blood filter as defined in claim 1, wherein each of the detectors is an ultrasonic sensor for sensing acoustic changes in the blood.

9. A blood filter as defined in claim 1, wherein each of the detectors is an impedance sensor for sensing impedance changes in the blood.

10. A blood filter as defined in claim 1, wherein each of the valves is a mechanical clamp driven by an electric signal.

11. A blood filter as defined in claim 1, wherein each of the valves is an piezoelectric element driven by an electric signal.

12. The blood filter of claim 1 wherein the number of separate blood paths is 11.

13. A blood filter for removing unwanted particles from blood, comprising
   a housing having a blood inlet area for receiving blood to be filtered, a blood outlet area, and a blood return area for returning blood having unwanted particles to a reservoir;
   a plurality of blood paths extending in a downstream direction from the inlet area to the outlet area of the housing and adapted to flow blood therethrough;
   a first array of detectors attached to an upstream portion of the blood paths for detecting unwanted particles in the blood flowing trough the blood paths;
   a first array of valves attached to the blood paths downstream from the first array of detectors for closing selected ones of the blood paths when the unwanted particles are detected by the first array of detectors;
   a second array of detectors attached to the blood paths downstream from the first array of valves for detecting unwanted particles in the blood flowing through the blood paths; and
   a second array of valves attached to the blood paths downstream from the second array of detector for closing selected ones of the blood paths when the unwanted particles are detected by the second array of detectors; and
   a third array of detectors attached to the blood paths downstream from the second array of valves for detection unwanted particles in the blood flowing through the blood paths.

14. A blood filter as defined in claim 13, further comprising:
   a first plurality of return conduits connected to the blood paths between the first array of detectors and first array of valves and extending to the blood return area of the housing for flowing blood having unwanted particles to the reservoir;
   a fourth array of detectors adjacent to the first plurality of return conduits for monitoring the unwanted particles in the blood flowing therethrough;
   a third array of valves in operable relationship with the first plurality of return conduits for opening selected ones of the first plurality of return conduits;
   a second plurality of return conduits connected the blood paths between the second array of detectors and second array of valves and extending to the blood return area of the housing for flowing blood enable blood having unwanted particles to flow to the reservoir having unwanted particles to the reservoir;
   a fifth array of detectors adjacent to the second plurality of return conduits for monitoring the unwanted particles in the blood flowing therethrough; and
   a fourth array of valves in operable relationship with the second plurality of return conduits for opening selected ones of the second plurality of return blood to enable blood having unwanted particles to flow to the reservoir.

15. A blood filter as defined in claim 13, wherein the inlet area of the housing has a spiral structure to impart momentum to blood entering the housing so that the blood is distributed to the plurality of blood paths based on the momentum of the particles.

16. A blood filter as defined in claim 13, wherein an average number of blood paths closed at any one time is predetermined, and the inlet cross-sectional area of the housing is substantially the same as a sum of the cross-sectional areas of all of the plurality of blood paths less the cross-sectional areas of the predetermined average number of blood paths closed at the same time by the valves.

17. A blood filter as defined in claim 13, further comprising a third array of detectors attached to the blood paths downstream from the second array of valves for detecting unwanted particles in the blood flowing through the blood paths.

18. A method or removing unwanted particles from blood, comprising the steps of:
   supplying blood to an inlet of a blood filter having a blood outlet and a blood return;
   concurrently flowing the blood through a plurality of separate blood paths extending from the inlet to the outlet of the blood filter;
   detecting unwanted particles in the blood flowing through the blood paths and generating signals upon detection of particles;
   closing selected ones of the blood paths based on the signals and returning the blood to a reservoir through the blood return; and
   limiting the number of the closed blood paths to ensure an adequate blood flow from the inlet to the outlet of the filter.

19. The method of claim 18 wherein the limiting step includes monitoring the number of th closed blood paths and preventing further closure of additional blood paths.

20. A blood filter for removing unwanted particles from blood, comprising:

a housing having a blood inlet are for receiving blood to be filtered, a blood outlet area, and a blood return area for returning blood having unwanted particles to a reservoir;

a plurality of separate blood paths extending from the inlet area to the outlet area of the housing for flowing the blood therethrough, wherein each of the blood paths includes;

a detector adjacent to the blood path for detecting unwanted particles in the blood flowing through the blood path;

a valve in operable relationship with the blood path for closing the blood path when an unwanted particle is detected by the detector;

wherein the inlet area of the housing has a spiral structure to impart momentum to blood entering the housing so that the blood is distributed the plurality of blood paths based on the momentum of the particles.

* * * * *